United States Patent
Kondo et al.

(10) Patent No.: US 6,679,876 B2
(45) Date of Patent: Jan. 20, 2004

(54) CORNEAL SURGERY APPARATUS

(75) Inventors: Naoyuki Kondo, Anjyo (JP);
Kazunobu Kojima, Gamagori (JP);
Satoshi Imaizumi, Anjyo (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 09/982,780

(22) Filed: Oct. 22, 2001

(65) Prior Publication Data

US 2002/0049430 A1 Apr. 25, 2002

(30) Foreign Application Priority Data

Oct. 20, 2000 (JP) .................................... 2000-327027

(51) Int. Cl.$^7$ .................................................. A61F 9/008
(52) U.S. Cl. .................................. 606/5; 606/4; 606/10
(58) Field of Search .................................. 606/4, 5, 10

(56) References Cited

U.S. PATENT DOCUMENTS

| | | | |
|---|---|---|---|
| 4,838,266 A | * 6/1989 | Koziol et al. | 606/5 |
| 5,395,356 A | * 3/1995 | King et al. | 606/4 |
| 5,507,799 A | 4/1996 | Sumiya | |
| 5,556,395 A | 9/1996 | Shimmick et al. | |
| 5,613,965 A | * 3/1997 | Muller | 606/5 |
| 5,634,920 A | * 6/1997 | Hohla | 606/5 |
| 5,637,109 A | 6/1997 | Sumiya | |
| 5,651,784 A | * 7/1997 | Klopotek | 606/5 |
| 5,713,892 A | 2/1998 | Shimmick | |
| 5,800,424 A | 9/1998 | Sumiya | |
| 5,906,608 A | 5/1999 | Sumiya | |
| 6,033,075 A | 3/2000 | Fijieda et al. | |
| 6,056,740 A | * 5/2000 | Shimmick | 606/5 |
| 6,063,072 A | * 5/2000 | Muller | 606/5 |
| 6,159,202 A | 12/2000 | Sumiya et al. | |
| 6,203,539 B1 | 3/2001 | Shimmick et al. | |
| 6,319,247 B1 | * 11/2001 | Hofer et al. | 606/5 |
| 2002/0013573 A1 | * 1/2002 | Telfair et al. | 606/5 |
| 2002/0151878 A1 | * 10/2002 | Shimmick et al. | 606/5 |

FOREIGN PATENT DOCUMENTS

EP          628298 A1  * 12/1994  ............. A61F/9/00

* cited by examiner

Primary Examiner—Lee Cohen
Assistant Examiner—Henry M. Johnson, III
(74) Attorney, Agent, or Firm—Rader, Fishman & Grauer PLLC

(57) ABSTRACT

The present invention is intended to provide a corneal surgery apparatus which enables a surgical operator to accurately ablate a cornea in part. The corneal surgery apparatus for ablating part of a cornea by irradiating a laser beam onto the cornea of a patient's eye comprises an irradiation optical system for irradiating the laser beam emitted from a laser light source onto the cornea, an aperture, which is disposed in the irradiation optical system, profiling a cross-sectional region of the beam perpendicular to an optical axis of the irradiation into one or more small regions, and correcting device for correcting an intensity distribution of the laser beam, which is changed when the beam passes through the aperture, to a specified intensity distribution.

9 Claims, 7 Drawing Sheets

CORNEAL SURGERY APPARATUS

BACKGROUND OF THE INVENTION

1. Field of the Invention present invention relates to a corneal surgery apparatus for correcting a refractive power of an eye and removing an affected portion of a cornea by ablating part of the cornea.

2. Description of Related Art

PRK (Photorefractive Keratectomy) is a surgical operation in which part of corneal tissue (a corneal stroma and the like) is ablated with a laser beam to correct a refractive error of an eye, and PTK (Phototherapeutic Keratectomy) is a surgical operation in which an affected portion of a cornea is removed. As for those two types of operations, there are three methods to ablate a corneal region intended to be removed: a one-shot irradiation method under which a laser beam of which cross-sectional shape perpendicular to an optical axis of irradiation is a large circle (a large spot) is irradiated at one shot, a slit scan method under which a laser beam of which cross-sectional shape is rectangular is irradiated to scan at least in one direction, and a spot scan method under which a laser beam of which cross-sectional shape is a small circle (a small spot) is irradiated to scan two-dimensionally.

Also, in order to change the cornea in an asymmetric shape such as irregular astigmatism to being symmetrical such as spherical or toric shapes, under the one-shot irradiation method and the slit scan method as disclosed in U.S. Pat. Nos. 6,203,539 and 5,906,608 corresponding to Japanese Patent Unexamined Publication No. HEI09(1997)-266925 and others, a laser beam, of which cross section is profiled (restricted) into a circular or rectangular small region with a circular- or rectangular-shaped aperture, is irradiated to remove an asymmetric component of the cornea.

Under the methods described above, however, diffraction occurs when the laser beam passes through the aperture and the like, and the diffraction makes an intensity distribution (energy distribution) of the laser beam approximately concave-shaped indicating that the peripheral part of the beam has stronger intensity than the central part. Then, repeated irradiation of the laser beam having this intensity distribution may end up obtaining an inaccurate result of ablation.

SUMMARY OF THE INVENTION

The present invention has been made in view of the above circumstances and has an object to overcome the above problems and to provide a corneal surgery apparatus which enables a surgical operator to accurately ablate a cornea in part.

To achieve the objects and in accordance with the purpose of the present invention, as embodied and broadly described herein, a corneal surgery apparatus for ablating part of a cornea by irradiating a laser beam onto the cornea of a patient's eye comprises an irradiation optical system for irradiating the laser beam emitted from a laser light source onto the cornea, an aperture, which is disposed in the irradiation optical system, profiling a cross-sectional region of the beam perpendicular to an optical axis of the irradiation into one or more small regions, and correcting means for correcting an intensity distribution of the laser beam, which is changed when the beam passes through the aperture, to a specified intensity distribution.

In another aspect of the present invention, a corneal surgery apparatus for ablating part of a cornea by irradiating a laser beam onto the cornea of a patient's eye comprises an irradiation optical system for irradiating the laser beam emitted from a laser light source onto the cornea, an aperture, which is disposed in the irradiation optical system, profiling a cross-sectional region of the beam perpendicular to an optical axis of irradiation into one or more small regions, and an optical member correcting an intensity distribution of the laser beam, which is changed when the beam passes through the aperture, to a specified intensity distribution, the optical member attached to the aperture on a side of the cornea.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
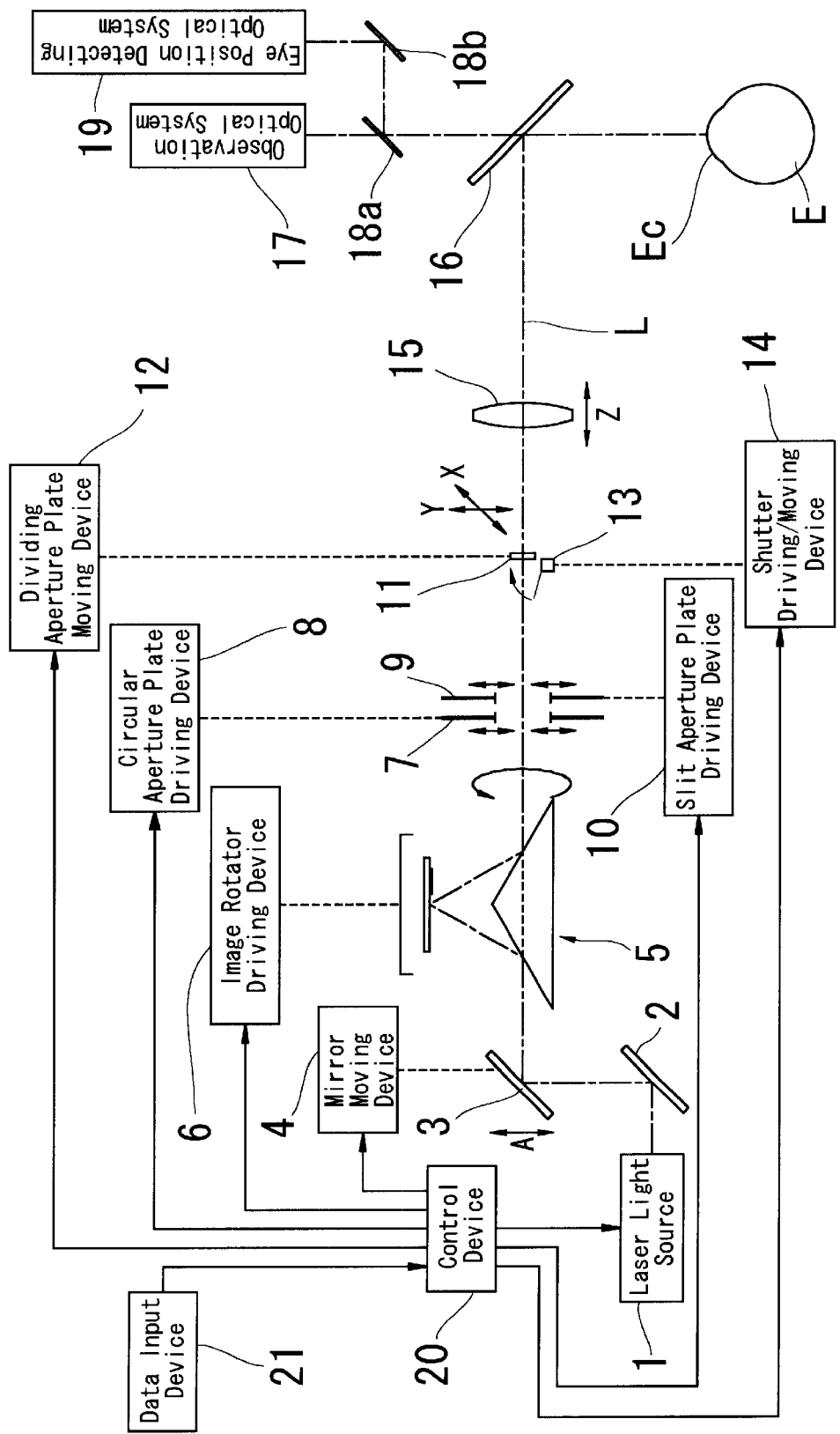
FIG. 1 is a view showing a schematic configuration of an optical system and a control system of a corneal surgery apparatus consistent with a preferred embodiment of the present invention.

A detailed description of one preferred embodiment of a corneal surgery apparatus embodying the present invention will now be given referring to the accompanying drawings. FIG. 1 is a view showing a schematic configuration of an optical system and a control system of a corneal surgery apparatus consistent with a preferred embodiment of the present invention.

Figure 2:
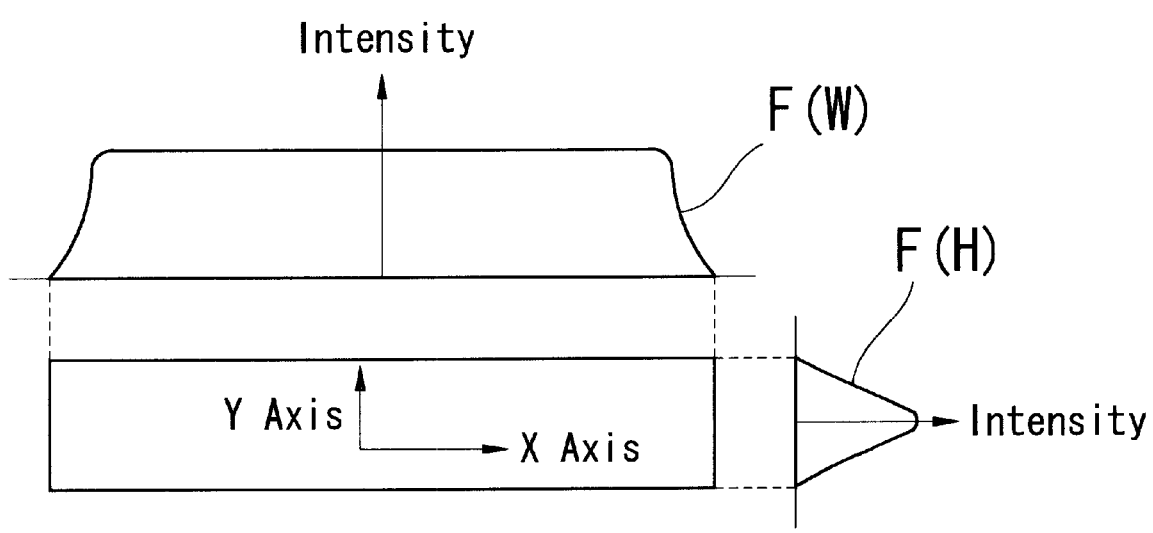
FIG. 2 is a view showing a typical shape of an intensity distribution of an excimer laser beam.

The present embodiment employs a laser light source 1 emitting an excimer laser beam having a pulse wave with a wavelength of 193 nm. As shown in FIG. 2, a typical cross-sectional shape of the laser beam orthogonal to an optical axis L of irradiation is a narrow rectangle. Also, an intensity distribution (energy distribution) of the laser beam shows an approximately uniform distribution F(W) in a longitudinal direction (the direction of an x axis) of the cross section and the Gaussian distribution F(H) in a direction perpendicular to the longitudinal direction (the direction of a y direction). It should be noted that the cross section of the laser beam emitted from the laser light source 1 may be made to form a desired rectangular shape by beam shaping means such as an expander lens, if necessary.

The laser beam emitted from the light source 1 is reflected by a plane mirror 2 to be deflected, and it is further reflected by a plane mirror 3 to be deflected. The mirror 3 is moved by a mirror moving device 4 in a direction of an arrow A along the optical axis L to have the laser beam make a parallel movement in the direction of the Gaussian distribution (reference should be made to U.S. Pat. No. 5,507,799 corresponding to Japanese Patent Unexamined Publication No. HEI4(1992)-242644 for details).

An image rotator 5 is rotationally driven on the optical axis L by an image rotator driving device 6 so that the laser beam reflected by the mirror 3 is rotated around the optical axis L (reference should be made to U.S. Pat. No. 5,637,109 corresponding to Japanese Patent Unexamined Publication No. HEI6(1994)-114083 for details).

An opening region (opening diameter) in a circular aperture plate 7 is changed by a circular aperture plate driving device 8 so as to restrict an ablation zone of a cornea Ec. Further, an opening region (opening width) in a slit aperture plate 9 is changed by a slit aperture driving device 10 so as to restrict the ablation zone of the cornea Ec, and a direction of the opening of the slit aperture is also changed as it is rotated on the optical axis L. A projecting lens 15 projects images of the opening regions in the circular aperture plate 7 and the slit aperture plate 9 on the cornea Ec of a patient's eye E so as to define the ablation zone.

Figure 3A:
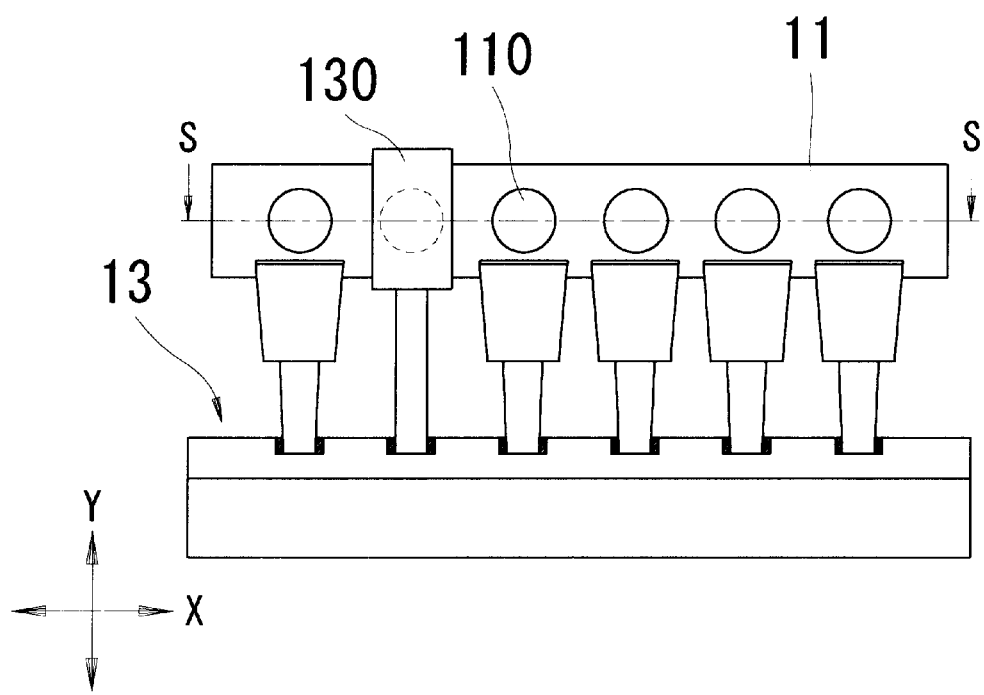
FIGS. 3A and 3B are views showing schematic configurations of a dividing aperture plate and a shutter device.

A dividing aperture plate 11, as combined with a shutter device 13, selectively divides the cross section of the laser beam in the longitudinal direction (the direction of the x axis). When the dividing aperture plate 11 is viewed from the side of the light source 1, a plurality of small circular apertures 110 (six apertures in the present embodiment) having the approximately same size and shape are arranged side by side, as shown in FIG. 3A. The lens 15 projects an image of the opening region of each of the small apertures 110 on the cornea Ec, and the cross section of the beam is profiled (restricted) into a small region (small regions). The narrow rectangular cross section of the beam can be selectively divided in the longitudinal direction to be irradiated by selectively covering and uncovering those small apertures 110 with each of shutter plates 130 of the shutter device 13.

Figure 3B:
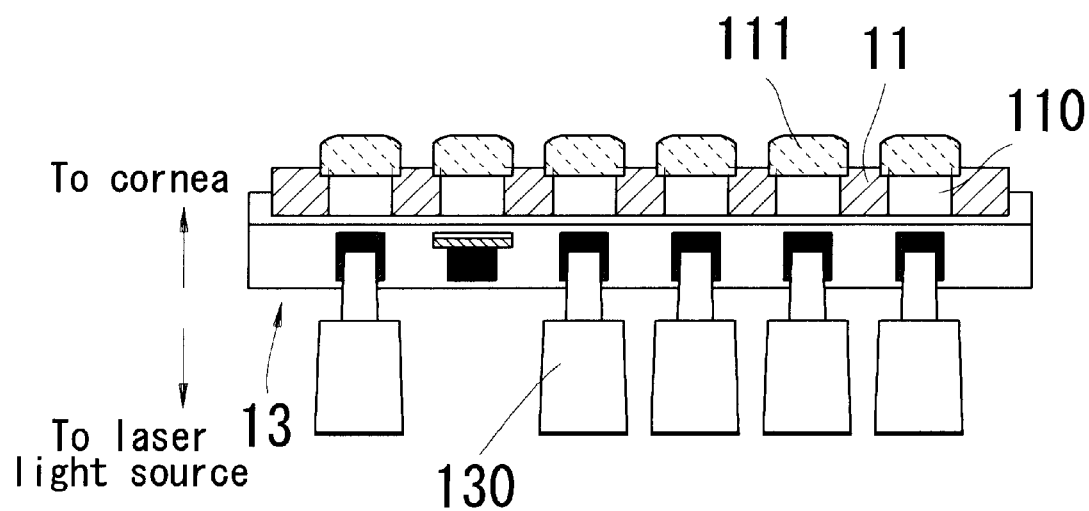
Figure 4:
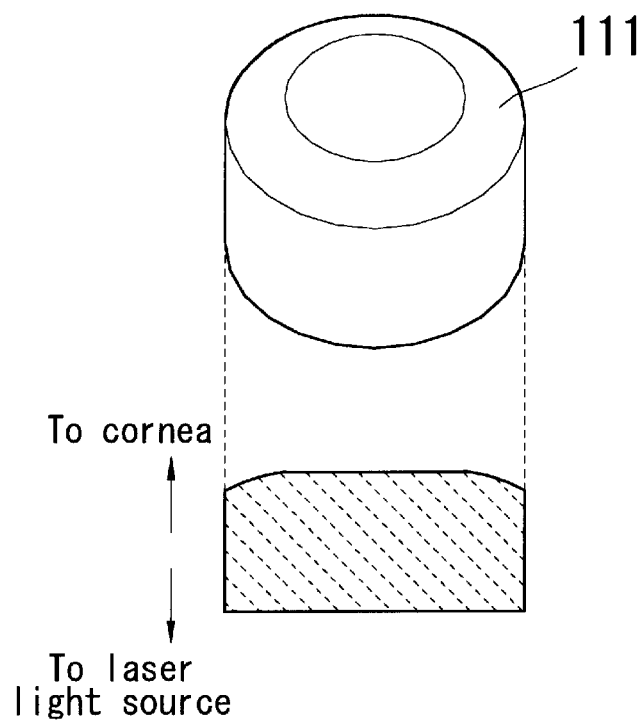
FIG. 4 is a view showing a shape of a window member.

As shown in FIG. 3B, each of the small apertures 110 is provided with a window member 111 on the side of the cornea Ec for correcting the intensity distribution of the laser beam affected by diffraction occurring when the laser beam passes through the small aperture(s) 110. Each of the window members 111 having a flat surface on the side of the small aperture(s) 110 (the side of the laser light source 1) and a non-spherical surface on the side of the cornea Ec is a transparent optical member (see FIG. 4). In the present embodiment, the window member 111 is made of synthetic fused quartz. FIG. 3B is a cross-sectional view of FIG. 3A observed from an S direction.

Figure 5:
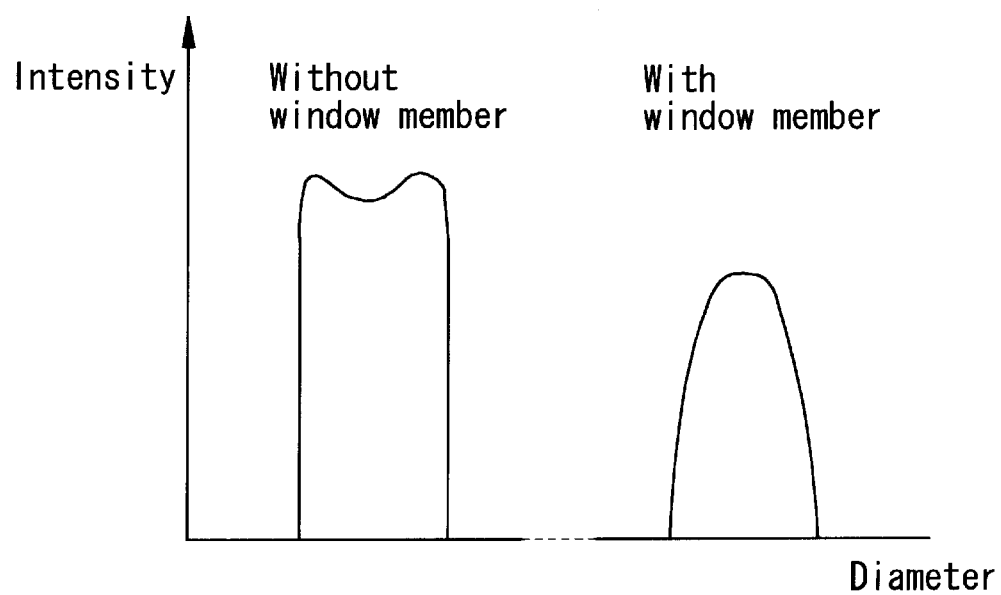
FIG. 5 is a graph showing a difference in the intensity distributions of the laser beam when the window member is employed and not employed.

FIG. 5 is a graph showing a difference in the intensity distribution of the laser beam when the window member 111 is employed and not employed. When the window member 111 is not used, the intensity distribution takes the shape of a concave because diffraction occurring when the laser beam passes through the small aperture(s) 110 makes the intensity greater in the peripheral part of the beam than in the central part. On the other hand, when the window member 111 is used, it corrects the intensity distribution affected by diffraction so as to make the intensity in the peripheral part of the beam smaller than the central part. As a result, the intensity distribution takes the shape of an approximate convex (it may be possible to adjust the non-spherical surface on the side of the cornea Ec so that the intensity distribution becomes approximately uniform).

The dividing aperture plate 11 may be moved in the longitudinal direction (the direction of the x axis) of the cross section of the laser beam and in the direction perpendicular to the longitudinal direction (the direction of the y axis) by a dividing aperture plate moving device 12, and the shutter device 13 may be moved in the same directions by a shutter driving/moving device 14. Further, the shutter driving/moving device 14 opens and closes each of the shutter plates 130 by controlling the shutter device 13. It should be noted that the shutter plates 130 may be opened and closed by sliding rather than by rotating as shown in the figure.

A dichroic mirror 16 has a property which reflects the excimer laser beam having a wavelength of 193 nm and transmits visible light and infrared light. The laser beam passes through the lens 15, and is reflected by the dichroic mirror 16 to be deviated, so as to be guided to the cornea Ec. An observation optical system 17 having a binocular microscope is disposed above the dichroic mirror 16 (the description of the observation optical system 17 is omitted since it is irrelevant to the present invention). A dichroic mirror 18a has a property which reflects infrared light and transmits visible light. Reference numeral 18b is a plane mirror, and an eye position detecting optical system 19 detects a position of the patient's eye E (reference should be made to U.S. Pat. No. 6,159,202 corresponding to Japanese Patent Unexamined Publication No. HEI09(1997)-149914 for the details about the eye position detecting optical system 19).

A control device 20 controls the entire apparatus including the light source 1, the moving device 4, the driving devices 6, 8, and 10, the moving device 12, the driving/moving device 14, and so on. A data input device 21 is used to input ablation data for the cornea Ec and the like.

Next, operation of the apparatus having the configuration disclosed above, used for refractive surgery, will be described.

First, a description of a method for obtaining the ablation data (ablation amount data) for refractive surgery will be given by presenting an example of correction of myopic astigmatism with reference to FIGS. 6 and 7. The ablation data are obtained from a radius of a corneal curvature given by measuring a corneal shape and a radius of a corneal curvature given by converting an equivalent emmetropia corneal surface refractive power (reference should be made to U.S. Pat. No. 6,033,075 corresponding to Japanese Patent Unexamined Publication No. HEI11(1999)-342152 for the details about the method for obtaining these values).

Figure 6A:
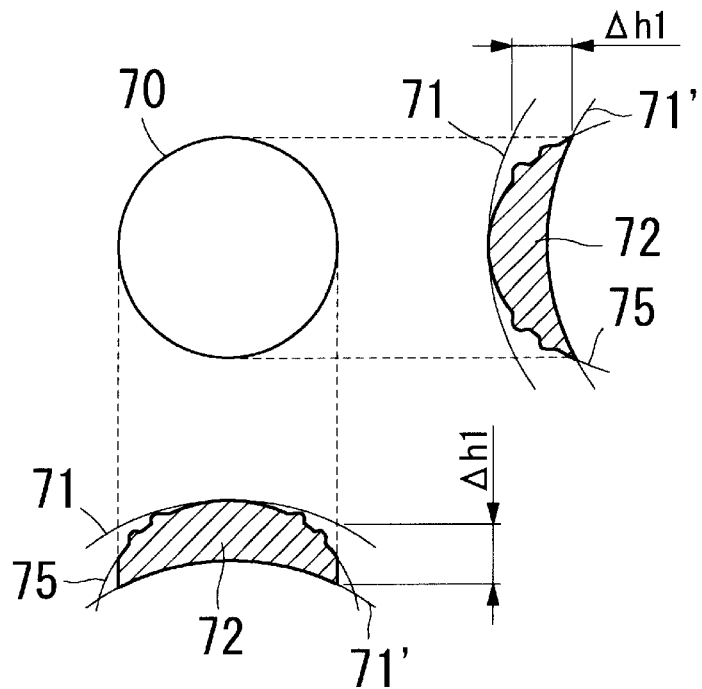
FIGS. 6A and 6B are views describing a method for obtaining ablation data for the cornea.
Figure 6B:
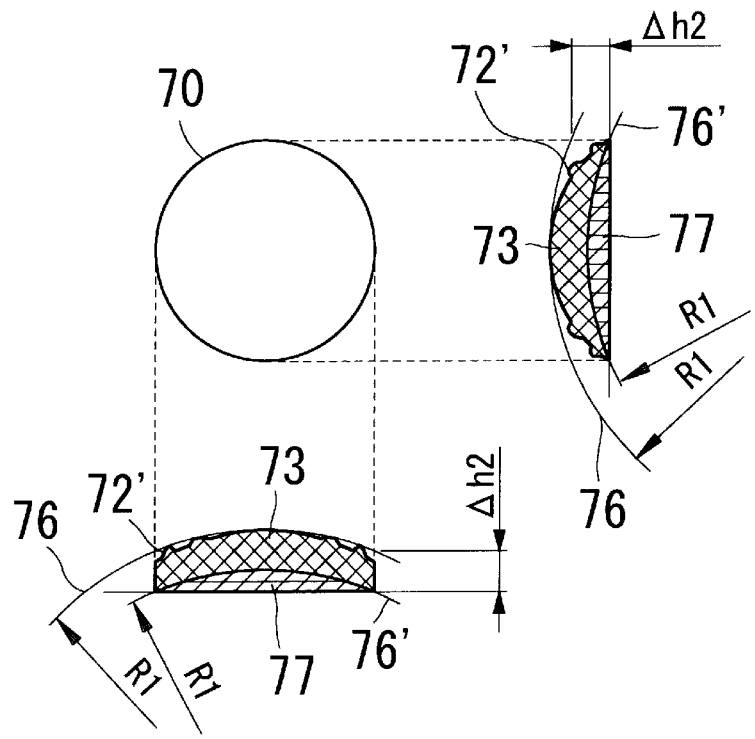

The radius of the corneal curvature given by measuring the corneal shape provides pre-operative corneal shape data showing a three-dimensional shape. Then, the radius of the corneal curvature given by converting an equivalent emmetropia corneal surface refractive power provides corneal shape data for desired correction (a post-operative corneal shape). Subsequently, total ablation data are obtained from the difference between the two sets of data mentioned above. That is, as shown in FIG. 6A, corneal shape data 71 for desired correction is shifted downward with respect to pre-operative corneal shape data 75 by Δh1 which is the maximum amount of the difference between those two sets of data in an optical zone 70 showing the ablation zone (the data obtained from this procedure gives corneal shape data 71'). Height distribution data obtained after shifting the corneal shape data 71 provides total ablation data 72, and three-dimensional shape data 72' for the height distribution is obtained as shown in FIG. 6B. It is preferable that the ablation data obtained at this point be processed by smoothing.

When the equivalent emmetropia corneal surface refractive power is not employed as distinct from the present embodiment, the ablation data may be obtained in the following way. The post-operative corneal shape data are obtained from refractive power correction data (determined based on a refractive power value given by subjective measurement and the like). Then, the post-operative corneal shape data are subtracted from the pre-operative corneal shape data given by measuring the corneal shape. The obtained value is found as the ablation data.

Figure 7A:
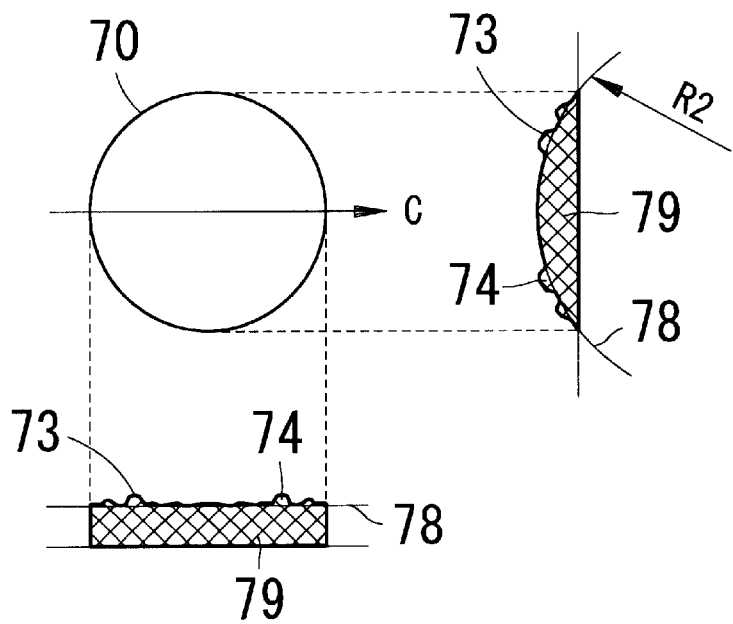
FIGS. 7A and 7B are views describing a method for obtaining ablation data for the cornea.

After the total ablation data 72 are obtained, ablation data for a spherical component are determined. For example, a minimum radius of a curvature R1 of a spherical shape 76 bordering on the outside of the three-dimensional shape data 72' of the total ablation data 72 is obtained with respect to the three-dimensional shape data 72' (see FIG. 6B). The spherical shape 76 having this minimum radius of the curvature R1 is shifted downward by Δh2 which gives spherical shape 76' so as to fall within the three-dimensional shape data 72'. Height distribution data obtained after shifting the spherical shape 76 are determined to be spherical ablation data 77. FIG. 7A shows residual ablation data 73 obtained by subtracting the spherical ablation data 77 from the total ablation data 72 (the three-dimensional shape data 72'). Then, ablation data for a cylindrical component are obtained from the residual ablation data 73.

For obtaining the ablation data for the cylindrical component, a direction C of an axial angle is determined. It can be determined by creating distribution data of the radius of the corneal curvature at each set of coordinates based on the shape of the total ablation data 72 and by determining a direction of the flattest curvature based on the distribution data. In FIG. 7A, the direction of the axial angle C is set at zero degree.

Figure 7B:
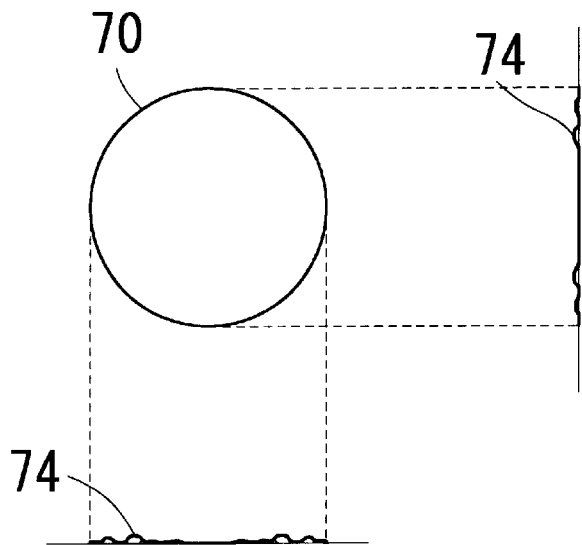

Next, with respect to the shape of the residual ablation data 73 illustrated in FIG. 7A, the maximum radius of the curvature R2 of a cylindrical shape 78, inscribed in the shape of the residual ablation data 73 is obtained with reference to the direction C of the axial angle. Height distribution data on the cylindrical shape 78 having the maximum radius of the curvature R2 are determined as cylindrical ablation data 79. FIG. 7B shows a reminder after subtracting the cylindrical ablation data 79 from the residual ablation data 73 mentioned above, and this reminder gives ablation data 74 for the irregular astigmatic component (an asymmetrical component).

The example of myopic correction has been described so far, but the preferred embodiment is not limited to this example. Each set of the ablation data for the spherical component and the cylindrical component for hyperopic correction can be obtained in the same manner so that an ablation amount in the peripheral part is made to be larger than in the central part.

In addition, the above description is only one example of a method for obtaining the ablation data for symmetrical and asymmetrical components, and there should be many other methods for obtaining them. For example, after the direction C of the astigmatic axial angle is obtained, the total ablation shape data may be analyzed into sections, for instance by 2 μm, in the direction of height so that the inscribed circle with respect to each of the sections is sequentially obtained in consideration of the direction C of the axial angle. In such a manner, the spherical and non-spherical components and their ablation data can be found. The ablation data for the asymmetrical component may be obtained by subtracting the ablation data for the spherical and non-spherical components as a rotationally symmetrical component and for the cylindrical component as a linearly symmetrical component from the total ablation data.

Incidentally, when a maximum ablation amount with respect to the entire optical zone 70 is in excess of an allowable ablation amount of the cornea Ec, the ablation amount should be corrected so that the maximum ablation amount falls within the allowable ablation amount by narrowing the optical zone 70 down.

Each set of the ablation data for the spherical (non-spherical) component, the cylindrical component, and the irregular astigmatic component is stored in memory within the control device 20 by using the input device 21. A position of a pupil center of the patient's eye E with respect to the data mentioned above is also inputted. The control device 20 determines the number of laser irradiation pulses and an irradiation power at each set of the coordinates on the cornea Ec based on the inputted ablation data. According to the number and the power thus determined, laser irradiation is controlled for performing refractive surgery.

When the ablation data and the position of the pupil center are entered by using the input device 21, the pupil center of the patient's eye E is obtained as a reference position for the surgical operation. Based on an image of an anterior part of the eye E photographed with a CCD camera which is disposed in the eye position detecting optical system 19 and is not illustrated in the figure, the position of the pupil center may be obtained in the following way: The first line horizontal to the pupil is obtained so as to run through an approximately center of the pupil. Then, the second line perpendicular to the first horizontal line is obtained so as to run through a midpoint between the two points where the first line and the edge of the pupil intersect. Next, the third line parallel to the second line, intersecting the edge of the pupil at two points, is obtained so as to run through the approximately center of the pupil. Then, the fourth line parallel to the first horizontal line is obtained so as to run through a midpoint between the two points where the third line and the edge of the pupil intersect. Finally, the point where the second line and the fourth line intersect indicates the pupil center. Also, it may be possible to take another way, in which the pupil center is determined based on a barycenter of the pupil. Further, an operator may simply observe the pupil with a surgical microscope to determine the pupil center. The position of the pupil center with respect to the ablation data is coincided with the position of the pupil center obtained by the eye position detecting optical system 19. Then, the control device 20 controls each of the driving devices and moving devices under the following method based on each of the ablation data for the spherical (non-spherical) component, the cylindrical component, and the irregular astigmatic component so that the cornea Ec is ablated.

In the case of myopic correction based on the ablation data for the spherical (non-spherical) surface, the ablation zone is restricted by the circular aperture plate 7. Then, the mirror 3 is moved in sequence so that the laser beam is moved in the direction of the Gaussian distribution. Every time the laser beam finishes moving on one surface (one scan), the timing of laser pulse and the rotation of the image rotator 5 are staggered so that the direction of the laser beam's movement (scanning) is changed (for example, in three directions each having space of 120 degrees). In such a manner, the zone restricted by the circular aperture plate 7 may be ablated approximately uniformly. By repeating this procedure ever time the size of the opening region in the circular aperture plate 7 is changed, the spherical (non-spherical) component can be ablated, whereby the central portion of the cornea can be ablated deeply, and the peripheral portion of the cornea can be ablated shallowly.

In the case of astigmatic correction based on the ablation amount data for the cylindrical component, the size of the opening region in the circular aperture plate 7 is fixed in accordance with the optical zone, and the opening width in the slit aperture plate 9 is changed in sequence. Also, the driving device 10 adjusts the direction of the opening in the slit aperture plate 9 in advance so that the opening width in the slit aperture plate 9 is changed in the direction of the steepest meridian. As in the case of myopic correction described above, the mirror 3 is moved in sequence so that the laser beam is moved in the direction of the Gaussian distribution for carrying out laser beam irradiation. Then, the direction of the laser beam's movement (scanning) is changed every time the laser beam completes one scan, whereby the zone restricted by the slit aperture plate 9 is ablated approximately uniformly. By repeating this procedure while the opening width in the slit aperture plate 9 is sequentially changed, the cylindrical component can be ablated.

Incidentally, when the symmetrical component (spherical (non-spherical) component and cylindrical component) is ablated, the dividing aperture plate 11 and the shutter device 13 are removed from an optical path of the laser beam.

The dividing aperture plate 11 and the shutter device 13 are placed on the optical path by the moving device 12 and the driving/moving device 14 respectively so that the asymmetrical component (the irregular astigmatic component) is ablated. When the mirror 3 is sequentially moved, the laser beam irradiated onto the cornea Ec is moved (to scan) in the direction of the Gaussian distribution. At this point, each of the shutter plates 130 of the shutter device 13 is selectively opened and closed, whereby only the laser beam passing through the small aperture(s) 110 uncovered with the shutter plate(s) 130 is irradiated onto the cornea Ec. Then, based on the ablation data for the irregular astigmatic component, a position of the dividing aperture plate 11 (and the shutter device 13) and the opening and closing of each of the shutter plates 130 are controlled at each position of the laser beam's movements caused by the mirror 3 (an image of the uncovered small aperture(s) 110 is displaced on the cornea Ec). In addition, the ablation amount at each position is controlled in accordance with irradiation time and the number of scanning. In such a manner, ablation of the irregular astigmatic component is carried out.

Figure 8:
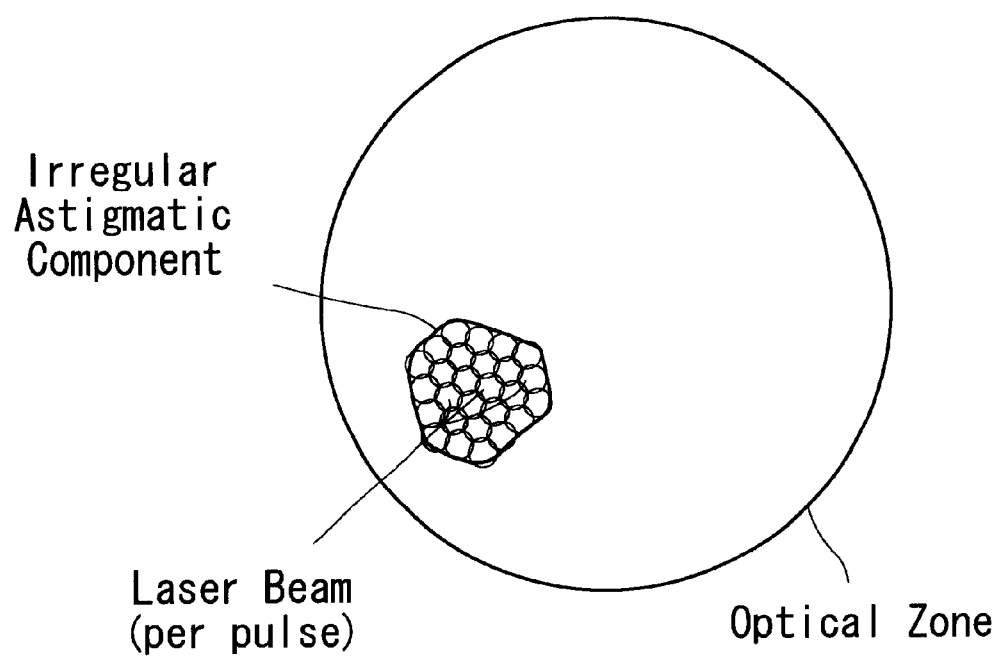
FIG. 8 is a view describing a method for ablating an irregular astigmatic component.

FIG. 8 illustrates the method for ablating the irregular astigmatic component. Although the irregular astigmatic component is ablated by superimposing a laser beam on another restricted to a small region, it is preventable to ablate an overlapping part deeply due to the use of the laser beam of which energy distribution takes the shape of a convex.

As described above, ablation of the symmetrical component (spherical (non-spherical) component and cylindrical component) is carried out separately from ablation of the asymmetrical component (irregular astigmatic component), whereby the total time necessary for a surgical operation can be reduced. Accordingly, it may be possible to perform the operation efficiently.

Further, according to the above description, ablation of the spherical (non-spherical) component is performed first, the cylindrical component is ablated second, and the asymmetrical component is done last. However, the order of the ablation procedure may be arbitrarily changed.

In addition, an example of a corneal surgery apparatus for which the slit scan method is employed is presented in the above description, but the present invention can be applied to a corneal surgery apparatus for which the one shot method and the like are employed. In this case, correcting means (an optical member) for correcting the intensity distribution of the beam should be attached to the aperture, profiling (restricting) the cross section of the beam into a small region, on the side of the cornea Ec. Then, the image of the opening region of the aperture is displaced by moving an image forming lens so that laser beam is irradiated.

Also, the window member 111 may be attached to the small aperture(s) 110 on the side of the laser light source 1, whereby a change in the intensity distribution of the beam may be predicted so as to be corrected before the laser beam passes through the small aperture(s) 110.

Further, as a data input device, it may be possible to employ an apparatus for determining an amount of corneal ablation, disclosed in such as U.S. Pat. No. 6,033,075 corresponding to Japanese Patent Unexamined Publication No. HEI11(1999)-342152.

As described above, the present invention enables a surgical operator to accurately ablate a corneal surface in part.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus for ablating a part of a cornea by irradiating a laser beam onto the cornea of a patient's eye comprising:

an irradiation optical system for irradiating the laser beam emitted from a laser light source onto the cornea, the irradiation optical system including a first irradiation optical system and a second irradiation optical system both to be used selectively, wherein the first irradiation optical system irradiates a relatively large spot beam, and the second irradiation optical system irradiates a relatively small spot beam;

a variable aperture, which is disposed in the first irradiation optical system, having a variable opening region and profiling a large cross-sectional area of the beam perpendicular to an optical axis of the irradiation into an intended area; and an image forming lens forming an image of the opening region of the variable aperture on the cornea;

a small aperture, which is disposed in the second irradiation optical system, having a fixed opening region and profiling the large cross-sectional area of the beam into a small area;

a non-spherical lens, which is disposed close to the small aperture, having a flat surface in a center part of the lens and a curved surface in a periphery part of the lens and correcting an intensity distribution of the laser beam, which is changed when the beam passes through the opening region of the small aperture, to a specified intensity distribution having a relatively large intensity in a center part of the beam and a relatively small intensity in a peripheral part of the beam; and moving means for moving the small aperture and the non-spherical lens inside and outside an optical path of the laser beam.

2. The corneal surgery apparatus according to claim 1, further comprising:

displacing means for displacing the image of the opening region of at least one of the apertures with respect to the optical axis of the irradiation;

data input means for inputting ablation data for the cornea; and control means for controlling the displacing means based on the inputted ablation data.

3. The corneal surgery apparatus according to claim 2, wherein the control means controls the displacing means based on the inputted ablation data for an asymmetrical component of the cornea.

4. The corneal surgery apparatus according to claim 2, further comprising a beam dividing device having an aperture plate including a plurality of the small apertures, a plurality of the non-spherical lenses, which are disposed close to each of the small apertures, and a shutter unit including a plurality of shutter plates for selectively covering and uncovering each of the small apertures, wherein the displacing means includes a moving unit which moves the beam dividing device with respect to the optical axis of the irradiation, and the control means controls the moving unit based on the inputted ablation data.

5. The corneal surgery apparatus according to claim 4, wherein the control means controls the shutter unit based on the inputted ablation data so that each of the shutter plates is selectively opened and closed.

6. The corneal surgery apparatus according to claim 1, wherein the non-spherical lens has a flat surface on a side of the laser light source and a non-spherical surface on a side of the cornea.

7. The corneal surgery apparatus according to claim 1, wherein the non-spherical lens corrects an approximately concave-shaped intensity distribution of the laser beam, which is changed when the beam passes through the opening region of the small aperture, to an approximately convex-shaped intensity distribution.

8. The corneal surgery apparatus according to claim 1, further comprising a beam moving unit which is disposed in the irradiation optical system and moves the laser beam in a direction of the Gaussian distribution with respect to the optical axis of the irradiation, wherein a cross-sectional shape of the beam perpendicular to the optical axis of the irradiation is rectangular, and the intensity distribution of the laser beam in a longitudinal direction of the cross section of the beam or in a direction perpendicular to the longitudinal direction is the Gaussian distribution.

9. The corneal surgery apparatus according to claim 1, wherein the image forming lens forms an image of the opening region of the small aperture on the cornea.

* * * * *